(12) United States Patent
Alsafhi et al.

(10) Patent No.: US 12,274,422 B1
(45) Date of Patent: Apr. 15, 2025

(54) APPARATUS FOR SANITIZING A FIBEROPTIC ENDOSCOPE

(71) Applicant: KING SAUD UNIVERSITY, Riyadh (SA)

(72) Inventors: Shahad Hussien Alsafhi, Riyadh (SA); Nora Fahad Alsudairi, Riyadh (SA); Khalid Abdullah Alhussaini, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/975,232

(22) Filed: Dec. 10, 2024

(51) Int. Cl.
| | | |
|---|---|---|
| *A61B 1/12* | (2006.01) | |
| *A61L 2/10* | (2006.01) | |
| *A61L 2/18* | (2006.01) | |
| *A61L 101/06* | (2006.01) | |

(52) U.S. Cl.
CPC ............... *A61B 1/121* (2013.01); *A61L 2/10* (2013.01); *A61L 2/18* (2013.01); *A61L 2101/06* (2020.08); *A61L 2202/11* (2013.01); *A61L 2202/122* (2013.01); *A61L 2202/123* (2013.01); *A61L 2202/14* (2013.01); *A61L 2202/24* (2013.01)

(58) Field of Classification Search
USPC .................................................. 250/455.11
See application file for complete search history.

(56) References Cited

U.S. PATENT DOCUMENTS

| | | | | |
|---|---|---|---|---|
| 5,770,739 | A * | 6/1998 | Lin .................. | C01B 15/14 525/61 |
| 6,010,662 | A * | 1/2000 | Lin .................. | A61L 2/208 422/292 |
| 6,495,100 | B1 * | 12/2002 | Lin .................. | A61L 2/208 422/33 |
| 8,474,204 | B2 | 7/2013 | Pan et al. | |
| 11,142,911 | B2 | 10/2021 | Chen et al. | |

(Continued)

OTHER PUBLICATIONS

Qing-Jun Chen, et al., "Seismic behaviour of a through-beam connection between concrete-filled steel tubular columns and reinforced concrete beams", Engineering Structures, 80: pp. 24-39 (2014); DOI: https://doi.org/10.1016/j.engstruct.2014.08.036. Abstract.

(Continued)

*Primary Examiner* — Kiet T Nguyen
(74) *Attorney, Agent, or Firm* — Nath, Goldberg & Meyer; Joshua B. Goldberg (57) ABSTRACT

An apparatus for sanitizing a fiberoptic endoscope includes an elongated box with an interior storage chamber and a cleaning piece connected to the exterior of the box. The cleaning piece and the box are arranged in-line with one another and are configured to receive a flexible endoscopic cable of a fiberoptic endoscope inside of them to sanitize and sterilize the cable. The flexible endoscopic cable is first inserted in the cleaning piece via a through opening of the cleaning piece. The cleaning piece includes a plurality of filtering media in its interior, each with a respective through hole. The flexible endoscopic cable is disinfected as it is moved through the filtering medium through holes. Having passed through the filtering media, the flexible endoscopic cable travels to the interior storage chamber of the box, where it is irradiated by an ultraviolet light source for sterilizing the flexible endoscopic cable.

20 Claims, 10 Drawing Sheets

(56) References Cited

U.S. PATENT DOCUMENTS

2001/0036670 A1* 11/2001 Fryer .................. G01N 31/226
                                                        422/62
2010/0170183 A1    7/2010  Abulaban
2023/0037589 A1    2/2023  Lee

OTHER PUBLICATIONS

Mengjiao Lv, et al., Experimental Study on Seismic Behavior of Newly Assembled Concrete Beam—Column Joints with L-Shaped Steel Bars, Applied Sciences 14:1262 (2024); DOI : https://doi.org/10.3390/app14031262.

Mohammad Manzoor Nasery, et al., "Effects of support type and geometric shape of steel tube on concrete-encased concrete-filled steel tube beam under low velocity impact", Structures, 47: pp. 781-799 (2023); DOI: https://doi.org/10.1016/j.istruc.2022.11.075. Abstract.

* cited by examiner

APPARATUS FOR SANITIZING A FIBEROPTIC ENDOSCOPE

TECHNICAL FIELD

The present disclosure relates to endoscopy, and more particularly, to an apparatus configured to sanitize a fiberoptic endoscope.

DISCUSSION OF THE RELATED ART

A fiberoptic endoscope is a medical device used for visually inspecting the pharyngeal area of a patient. The endoscope contains a handle component and a flexible fiberoptic endoscopic cable attached to the handle component. A camera and a light source are disposed at the end of the flexible endoscopic cable that is distal from the handle.

The camera of the endoscope is activated, the light source is turned on, and the end of the flexible endoscopic cable that contains the camera and the light source is inserted into the nasal cavity of a patient. Medical personal can then continue to insert the flexible endoscopic cable deeper, reaching pharyngeal area, inspecting the condition of the patient's pharynx through a monitor that displays a video feed from the camera.

The fiberoptic endoscope must be sterilized before being used again on another patient after such a procedure. However, the flexible endoscopic cable is delicate in nature. For example, numerous known sterilization techniques are not recommended to be performed on it due to the risk of damaging the cable. On the other hand, known sterilization methods that are considered safe for use on a flexible endoscopic cable require a long period of time to sterilize the fiberoptic endoscope in addition to that more than one person is required to complete the process. The waiting process significantly reduces the number of patients that the fiberoptic endoscope can be used on in a workday.

In addition, some medical clinics may not have the specialized equipment needed to safely sterilize a fiberoptic endoscope and/or the personnel trained to use said equipment.

SUMMARY

The present disclosure relates to an apparatus for sterilizing a fiberoptic endoscope. The apparatus of the present disclosure can be manufactured at a low cost and can be used to quickly and safely (e.g., gently) sterilize the flexible endoscopic cable of a fiberoptic endoscope.

The apparatus of the present disclosure for sterilizing a fiberoptic endoscope includes an elongated box with an interior chamber and a cleaning piece connected to the exterior of the box. The cleaning piece may alternatively be referred to as a cleaning assembly in this specification, and the terms are used interchangeably. The cleaning piece and the box are arranged in-line with one another, and are configured to receive the flexible endoscopic cable of a fiberoptic endoscope inside of them to sterilize the cable.

The cleaning piece is an elongated hollow structure with a through opening. The flexible endoscopic cable can be inserted into the through opening from a first end of the cleaning piece that is distal to the box. The flexible endoscopic cable can then be fed through the interior of the cleaning piece (via the through opening thereof), in a direction toward the box, until the flexible endoscopic cable reaches a second end of the elongated hollow structure, opposite to the first end thereof and proximal to the box.

A pair of filters, each having a disk-shape with an opening in the center of the disk, can be disposed in the interior of the elongated hollow structure. The filters can be spaced apart from one another. The pair of filters are configured to clean, disinfect and wipe the flexible endoscopic cable as a result of the contact (e.g., rubbing) that occurs when the flexible endoscopic cable passes through the center opening of each disk as the flexible endoscopic cable is fed through the interior of the cleaning piece. For example, a first one of the disks may rub (or apply) a disinfecting substance to the exterior surface of the flexible endoscopic cable as the cable passes through the center opening of the first disk. The other disk (downstream) may be configured to wipe the disinfecting substance (along with the disinfected bodily fluids/matter) from the exterior surface of the flexible endoscopic cable.

As the flexible endoscopic cable is inserted deeper into the apparatus of the present disclosure, the disinfected and wiped portion of the flexible endoscopic cable may exit the interior of the cleaning piece and enter the interior chamber of the elongated box.

The interior chamber of the box may contain an ultraviolet (UV) light source. The UV light source may be configured to be operated (e.g., turned on) when the flexible endoscopic cable is inserted in the interior chamber of the box to sterilize the flexible endoscopic cable.

The sterilization process by UV light is relatively quick and efficient. The flexible endoscopic cable can be pulled out of the interior chamber of the box (via the through opening of the cleaning piece) after it has been sterilized by the UV light. The fiberoptic endoscope can be used on another patient immediately after the sterilization process has been performed.

The configuration of the apparatus of the present disclosure for sterilizing an endoscopic examination tool enables a rapid and gentle sterilization of the flexible endoscopic cable.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Figure 1:
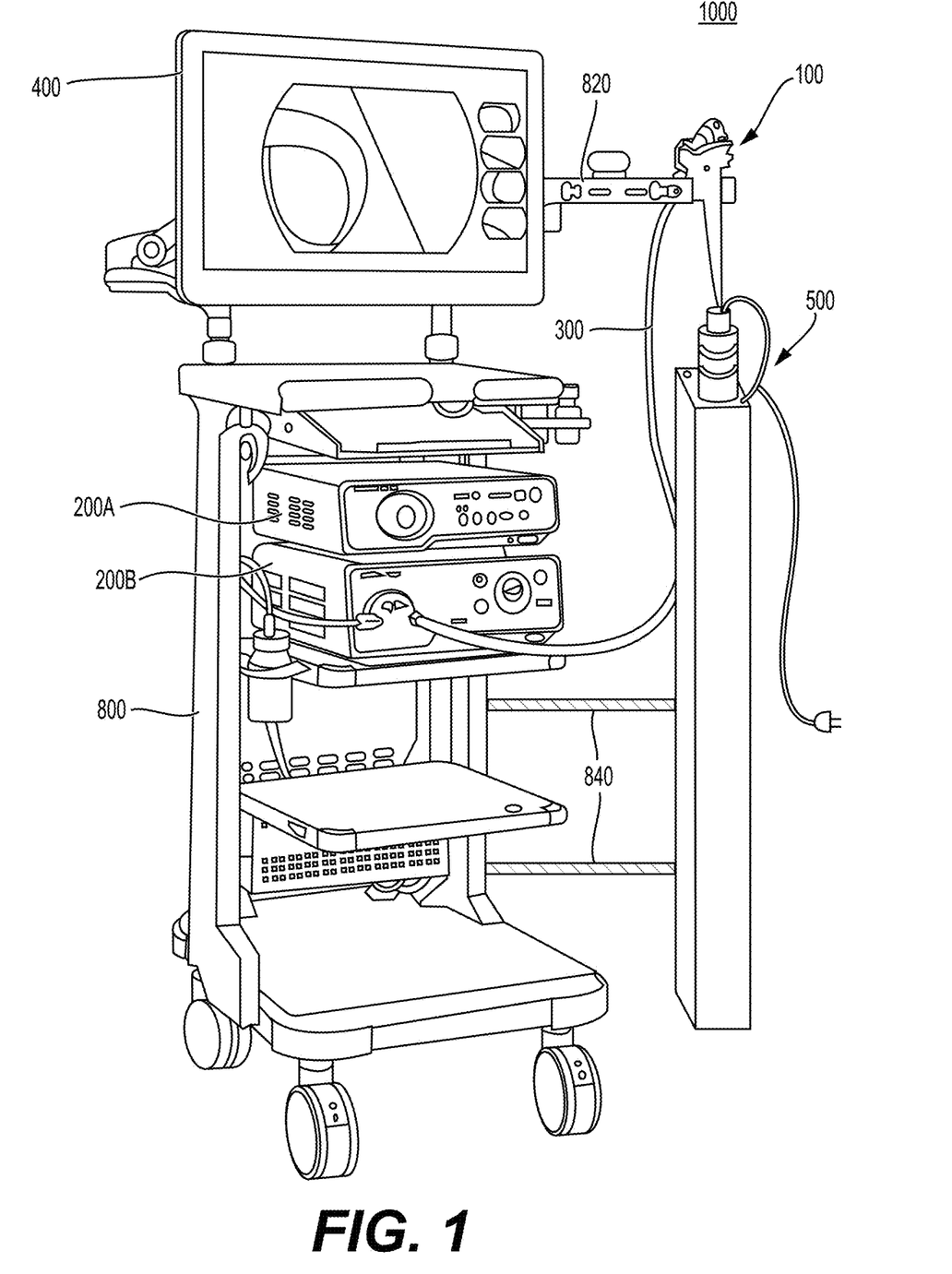
FIG. 1 is a perspective view illustrating a fiberoptic endoscopic examination station in accordance with an embodiment of the present disclosure.

The present subject matter is directed to a fiberoptic endoscopic examination station, and more particularly, to an apparatus for sterilizing a fiberoptic endoscope of a fiberoptic endoscopic examination station. FIG. 1 illustrates a perspective view illustrating a fiberoptic endoscopic examination station in accordance with an embodiment of the present disclosure. FIGS. 2-9 illustrate in more detail an apparatus included in the station of FIG. 1 for cleaning and sterilizing a fiberoptic endoscope included in the station of FIG. 1. More particularly, FIGS. 2-9 illustrate the fiberoptic endoscope and the apparatus for cleaning and sterilizing the fiberoptic endoscope in isolation from other components of the station of FIG. 1 for clarity purposes. The fiberoptic endoscope may also be referred to as an "endoscopic examination tool" in this specification, and the terms are used interchangeably.

Referring to FIG. 1, a fiberoptic endoscopic examination station 1000 includes a fiberoptic endoscope 100, hardware 200A, 200B configured to control an operation of the fiberoptic endoscope 100 based on a user's command, a cable 300 electrically connecting the fiberoptic endoscope 100 with the hardware 200A, 200B, a display panel 400 electrically connected to the hardware 200A, 200B and configured to illustrate images obtained by using the fiberoptic endoscope 100, an apparatus 500 for cleaning and sterilizing the fiberoptic endoscope 100, and a frame 800 configured to structurally support the hardware 200A, 200B and the fiberoptic endoscope 100.

For example, the frame 800 may include a first supporting arm 820 configured to structurally support the fiberoptic endoscope 100.

The endoscopic examination station 1000 may also include a pair of second supporting arms 840 protruding therefrom for connecting the apparatus 500 to the frame 800. Alternatively, the apparatus 500 might not be connected to the frame 800. When the apparatus 500 is not connected to the frame 800, the pair of second supporting arms 840 may be omitted, and the apparatus 500 may be connected to another structure near the frame 800 for stability purposes.

The fiberoptic endoscope 100 may be a conventional fiberoptic endoscope. As such, and with reference to FIG. 2, the fiberoptic endoscope 100 may include a head portion 120 and an elongated flexible endoscopic cable 140 connected to the head portion 120. The elongated flexible endoscopic cable 140 is illustrated in a hidden line in FIG. 2, indicating that the flexible endoscopic cable 140 is inserted inside of the apparatus 500. The fiberoptic endoscope 100 may include a camera and a light source disposed at a distal end 160 of the flexible endoscopic cable 140.

Figure 2:
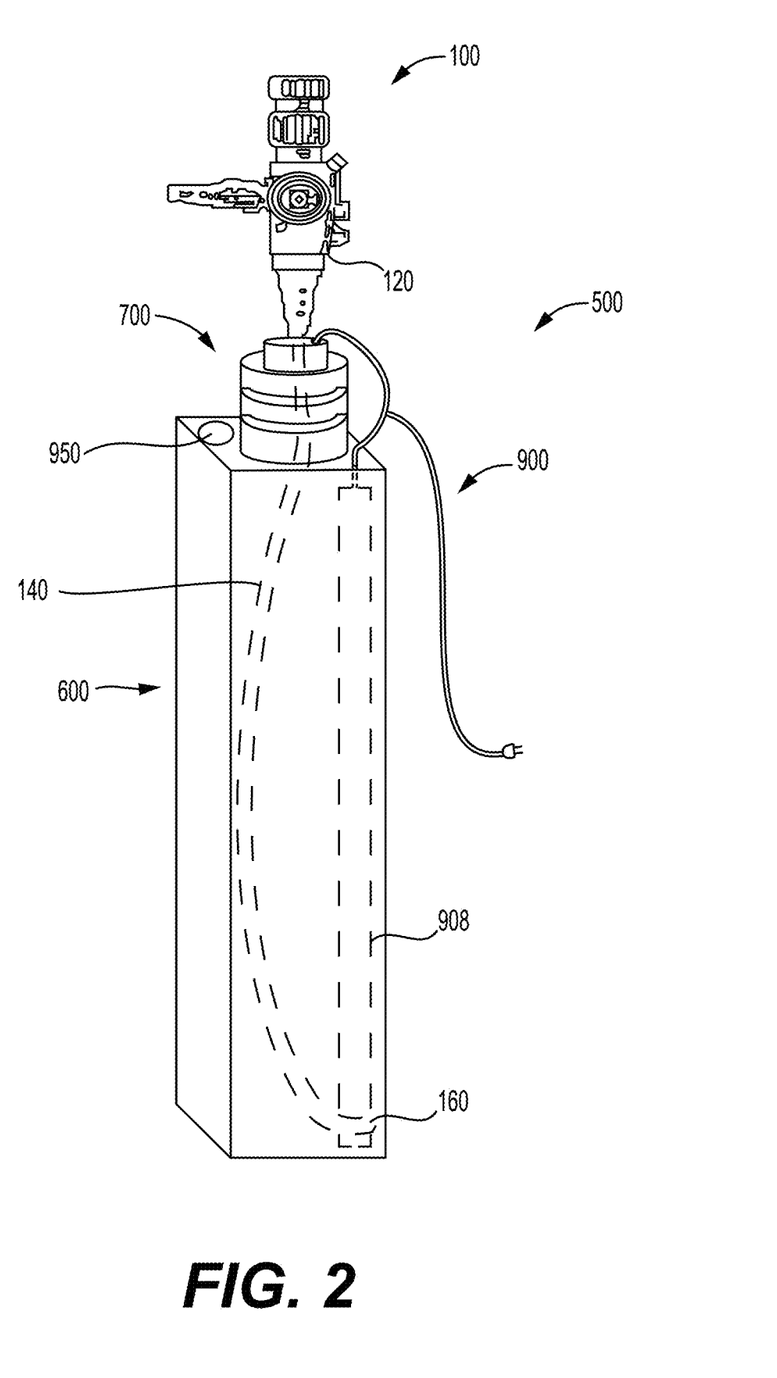
FIG. 2 is a perspective view illustrating a portion of a fiberoptic endoscopic examination tool included in the station of FIG. 1, and an apparatus for sterilizing the fiberoptic endoscopic examination tool included in the station of FIG. 1.
Figure 3:
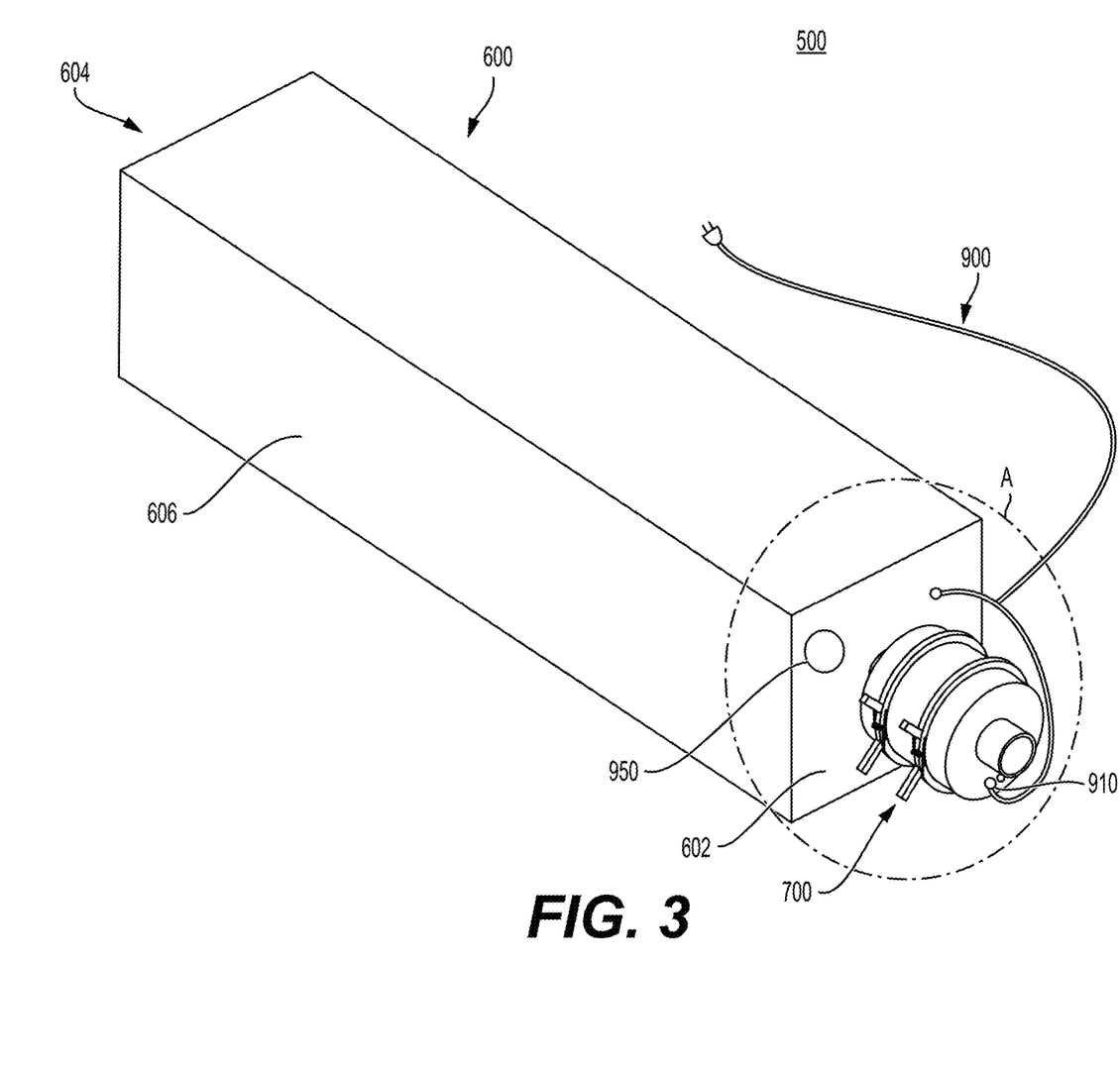
FIG. 3 is a perspective view illustrating the apparatus for sterilizing the endoscopic examination tool of the station of FIG. 1 in isolation.
Figure 4:
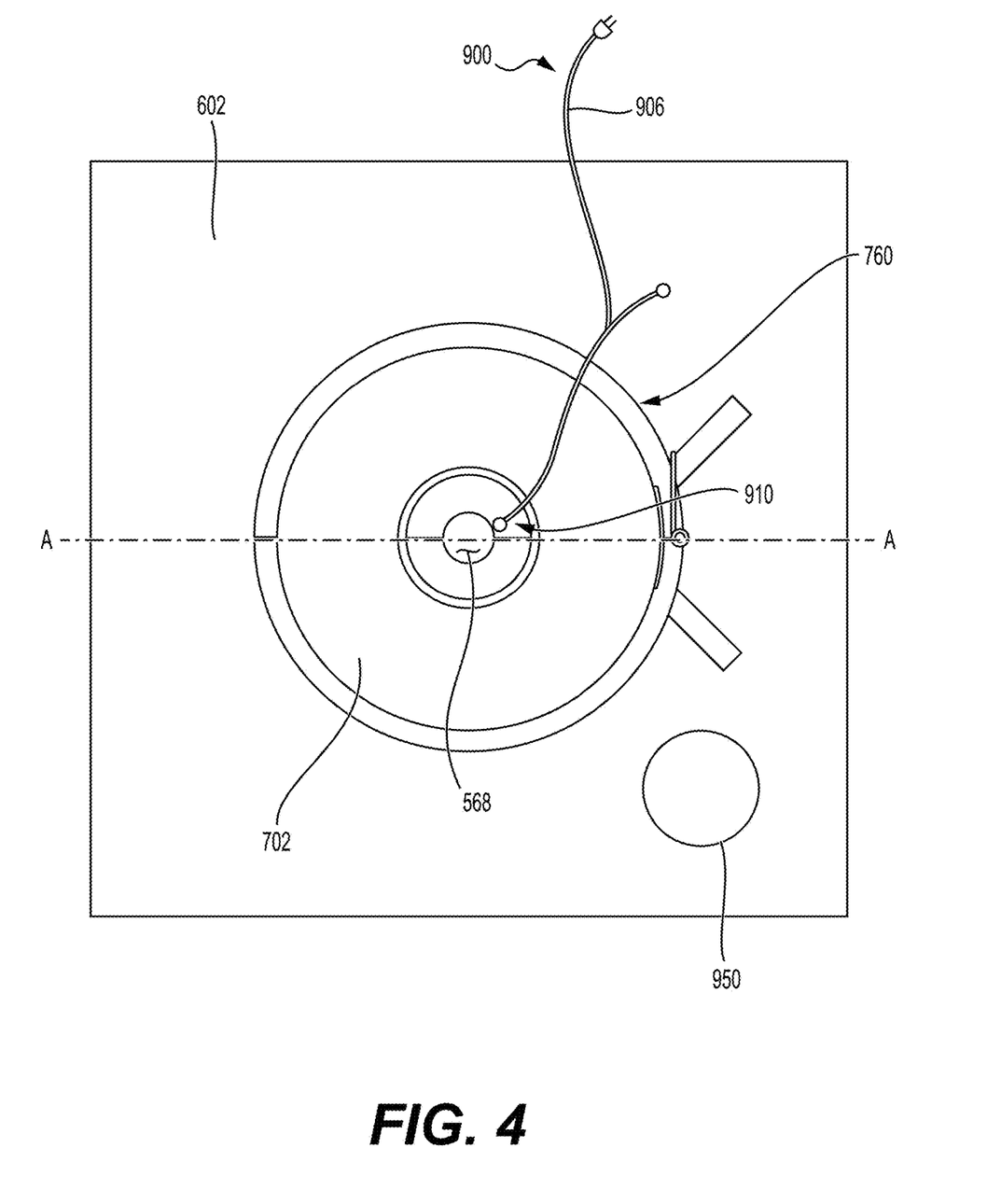
FIG. 4 is a side view illustrating the apparatus for sterilizing the endoscopic examination tool of the station of FIG. 1 in isolation.

The flexible endoscopic cable 140 is intended to be inserted through a nasal cavity of a patient into the pharynx of the patient for observation via the camera disposed at its distal end 160. The process of inserting the flexible endoscopic cable 140 into a patient's nasal cavity contaminates the flexible endoscopic cable 140 with bodily fluids and/or bodily matter. Therefore, the flexible endoscopic cable 140 must be sanitized/sterilized prior to subsequently being used again on another patient.

The apparatus 500 is configured to sanitize/sterilize the fiberoptic endoscope 100. More specifically, the apparatus 500 is configured to quickly and efficiently sanitize/sterilize the flexible endoscopic cable 140 of the fiberoptic endoscope 100 when the flexible endoscopic cable 140 is inserted in an interior of the apparatus 500.

The apparatus 500 will be described in detail below.

Referring to FIGS. 2-9, the apparatus 500 may include a container 600, a cleaning assembly 700 connected to the container 600, and an electrical circuit 900 for emitting ultraviolet irradiation inside of the container 600.

The container 600 includes a plurality of sidewalls defining an exterior of the container and an interior chamber of the container. For example, and with reference to FIG. 3, the sidewalls may include a first sidewall 602 disposed at a first end of the container 600, a second sidewall 604 disposed at a second end of the container 600, opposite to the first end thereof, and a plurality of sidewalls 606 (e.g., four sidewalls 606) connected to one another and to the first and second sidewalls 602, 604 to form interior chamber 608 (see FIG. 5) of the container 600.

A UV lamp 908 (see FIG. 5) is disposed in the interior chamber 608 and is usable for sterilizing the flexible endoscopic cable 140 in the interior chamber 608.

Figure 5:
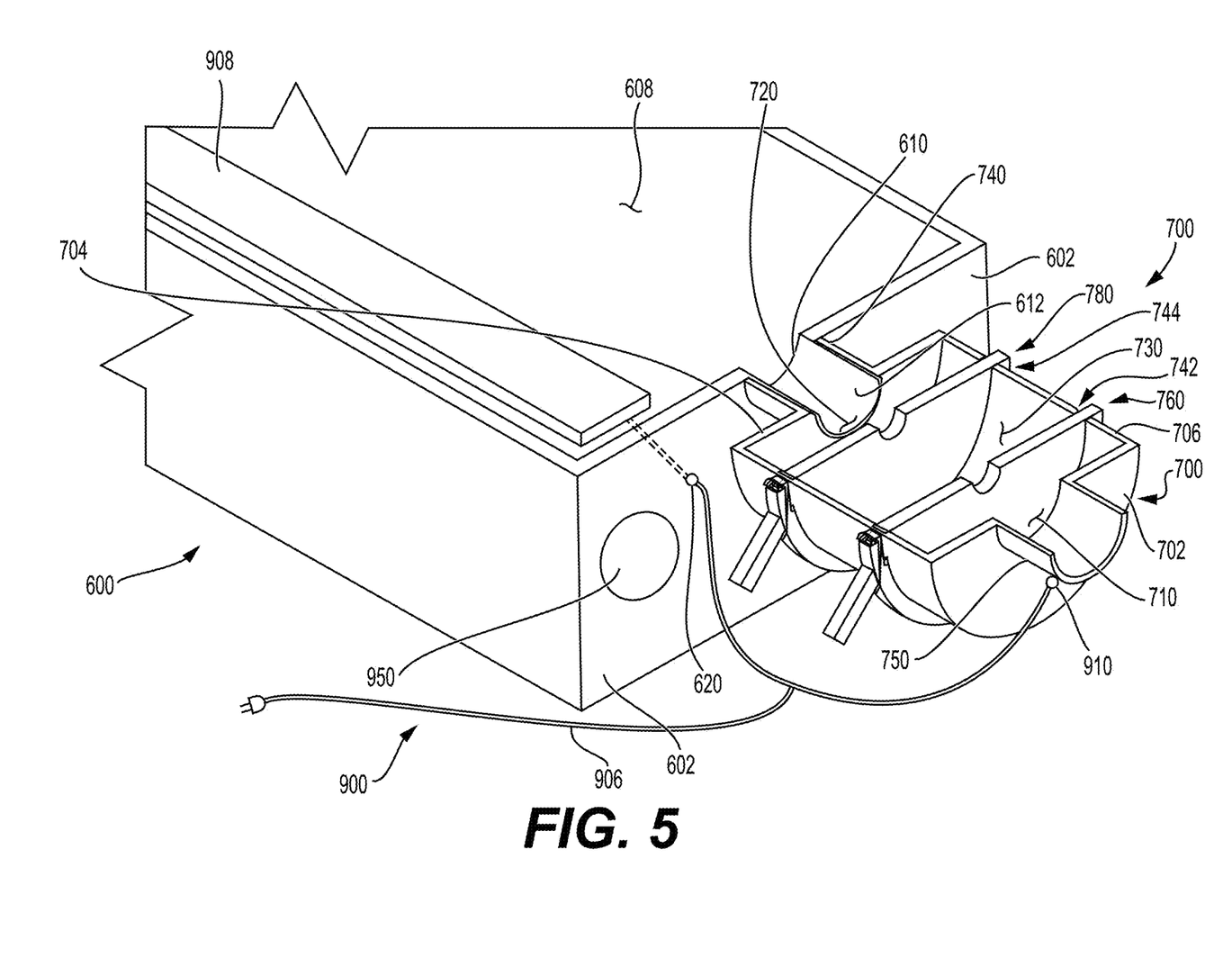
FIG. 5 is a perspective view illustrating the apparatus for sterilizing the endoscopic examination tool of FIG. 1 cut along line A-A of FIG. 4.

As more clearly illustrated in FIG. 5, the first sidewall 602 includes a through opening 610 (which may be referred to as a "second" through opening). Referring to FIG. 5, the container 600 may also include a first hollow connecting piece 612 extending from the first sidewall 602 thereof. The first hollow connecting piece 612 overlaps (or encircles) the second through opening 610 of the first sidewall 602 of the container 600. In other words, the first hollow connecting piece 612 is aligned with the second through opening 610 to provide access to the interior chamber 608 from an exterior of the container 600.

Figure 11:
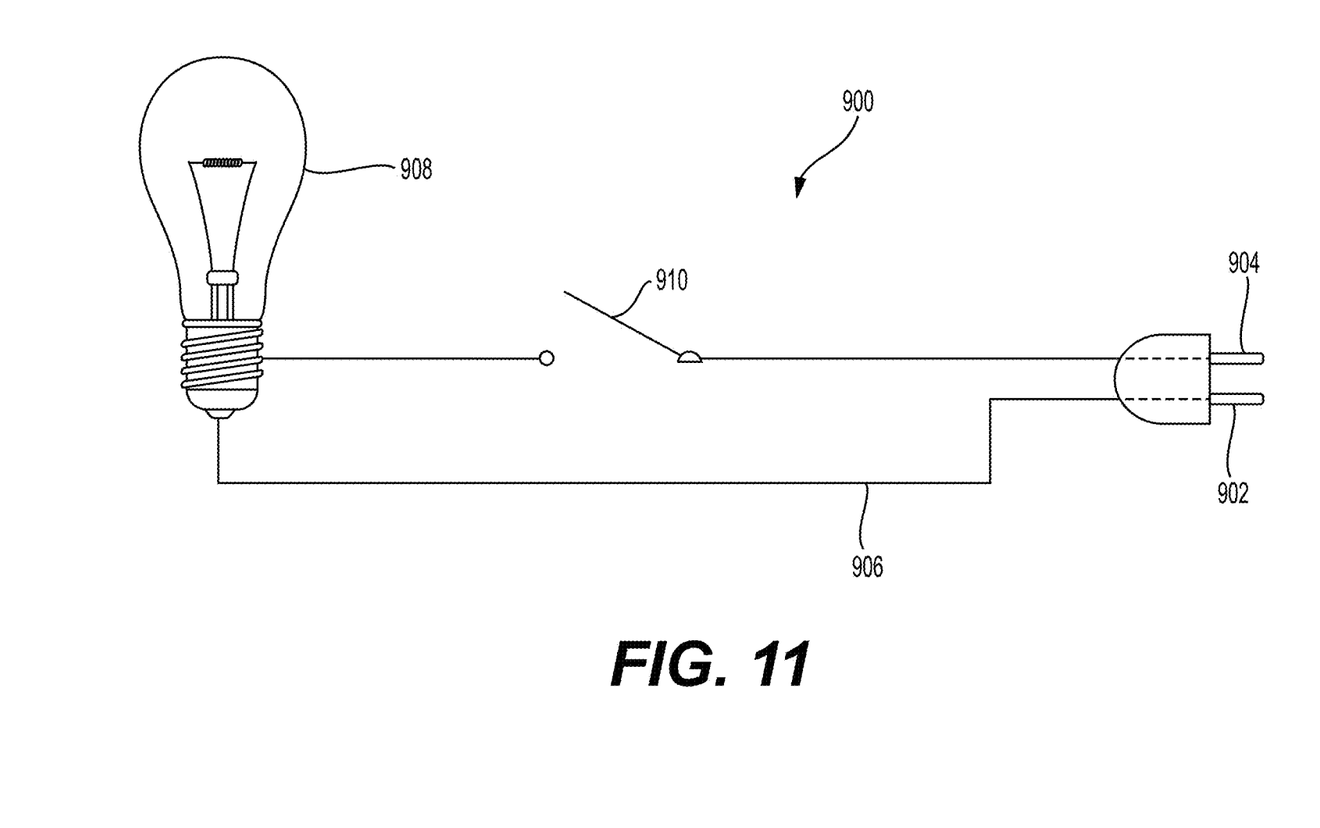
FIG. 11 is a diagram illustrating an electrical circuit for ultraviolet irradiation included in the apparatus for sterilizing the endoscopic examination tool of FIG. 1.

Referring to FIGS. 5 and 11, the electrical circuit 900 includes an electrical wire 906 having a first terminal end 902, a second terminal end 904, and a length between the first and second terminal ends 902, 904, an ultraviolet (UV) light source 908 electrically connected to the wire 906 along the length of said wire 906, and a switch 910 disposed along the length of the wire 906. The switch 910 is configured to selectively open and close the electrical circuit 900.

Referring to FIG. 5, the UV light source 908 is disposed in the interior chamber 608 and is configured to emit UV rays in the interior chamber 608 to sterilize the flexible endoscopic cable 140 in the interior chamber 608. The UV light source 908 may be configured to emit ultraviolet C (UVC) rays in the ultraviolet spectrum. UV light in general is effective for sterilizing contamination imparted on the flexible endoscopic cable 140 as result of being inserted in the nasal cavity reaching the pharyngeal area of a patient. UVC light, in particular, which has a wavelength in the range of about 180 to about 280 nm, is highly effective at sterilizing the flexible endoscopic cable 140 after use on a patient while being gentle on the exterior of the flexible endoscopic cable 140.

The UV light source 908 may include, for example, one or more incandescent light bulbs, one or more light emitting diodes (LEDs), one or more fluorescent lamps, one or more low vapor pressure mercury-based lamps, one or more pulsed-xenon lamps, etc., or a combination thereof.

The number, arrangement and/or shape of lamps/bulbs/diodes included in the UV light source 908 may be selected such that the UV light source 908 as a whole can disinfect the entire length of the flexible endoscopic cable 140 inserted in the interior chamber 608. The intensity of the UV light source 908 may be selected such that it can disinfect the flexible endoscopic cable 140 quickly or at least in a reasonable amount of time.

Figure 9:
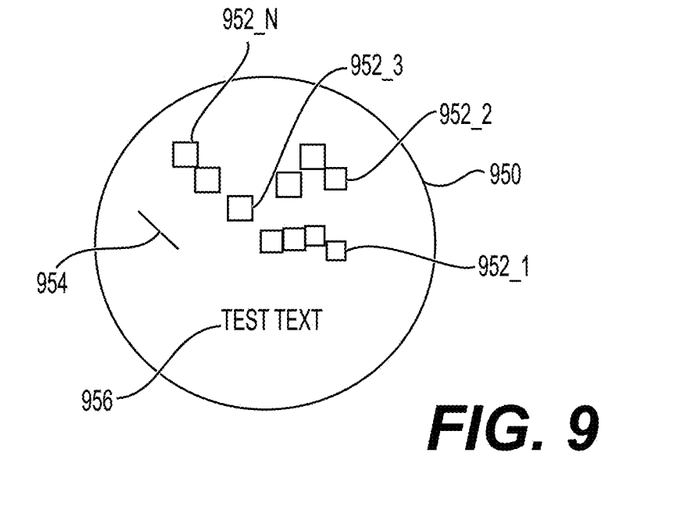
FIG. 9 is a top plan view illustrating a tag included in the apparatus for sterilizing the endoscopic examination tool of FIG. 1.
Figure 10:
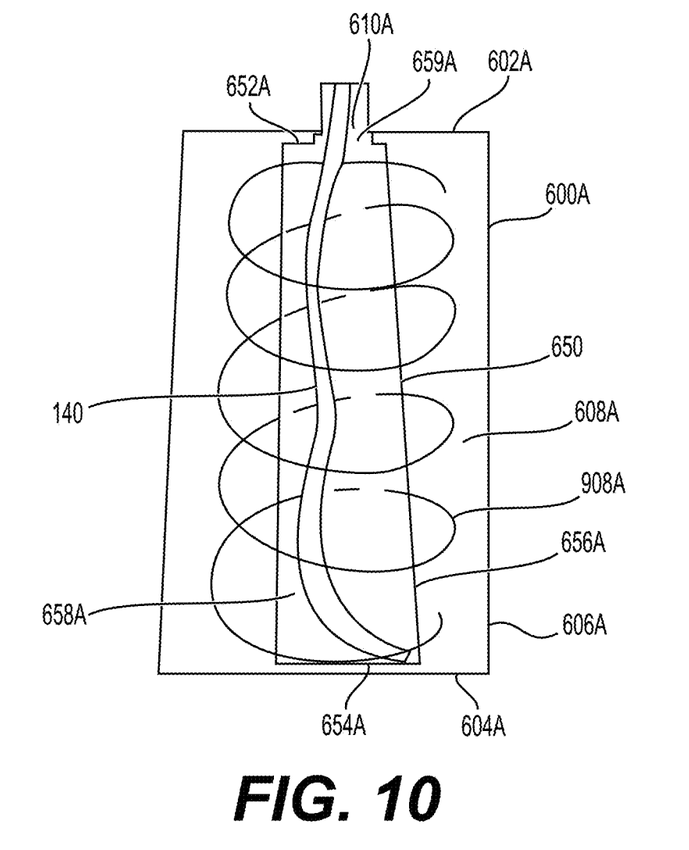
FIG. 10 is a side view illustrating a container included in an apparatus for sterilizing an endoscopic examination tool according to an embodiment of the present subject matter.

In an embodiment, as illustrated with referee to FIGS. 1-9 and 11, the UV light source 908 may have an elongated bar shape and may span an entire length of the interior chamber 608. In a different embodiment, as illustrated in FIG. 10, a UV light source 908A may have a helical shape that coils around a transparent elongated vessel 650 in an interior chamber 608A of a container 600A. The container 600A may be the same as container 600 except that the container 600A includes the transparent elongated vessel 650 inside.

The UV light source 908A may span an entire length of the interior chamber 608A of the container 600A.

The bar and helical shapes of the UV light sources 908, 908A are non-limiting. A UV light source of the present subject matter may have other shapes so long as the UV light source is capable of sterilizing the entire length of flexible endoscopic cable 140 inserted inside of the box. In addition, and irrespective of its shape, a UV light source need not necessarily extend along the entire length of the interior chamber of the container. The UV light source may be shorter than the length of the interior chamber of the container so long as it is capable of sterilizing the entire length of the flexible endoscopic cable 140 inserted in the box.

As indicated elsewhere in this specification, the embodiment of FIG. 10 includes the transparent elongated vessel 650 disposed in an interior chamber 608A of a container 600A, while the embodiment of FIGS. 1-9 and 11 omits the transparent inner elongated vessel from the interior chamber 608 of the container 600.

Referring to FIG. 10, the elongated vessel 650 is made of a transparent or translucent material such that it may convey UV irradiation therethrough. For this reason, the material elected for constructing elongated vessel 650 should have a high resistivity to structural degradation from exposure to UV light. For example, the inner container 650 may be made of translucent quartz glass, translucent conventional glass, and/or translucent elastomeric material (e.g., plastic material).

The elongated vessel 650 is disposed in the interior chamber 608A of the container 600A. The elongated vessel 650 is connected to the container 600A on the inside of the container 600A. For example, the elongated vessel 650 can be connected to one or more sidewall of the container 600 from the interior chamber 608A.

Referring to FIG. 10, the elongated vessel 650 includes a first sidewall 652A at a first end thereof, a second sidewall 654A at a second end thereof, opposite to the first end thereof, and a hollow body 656A extending between the first and second sidewalls 652A, 654A. The hollow body 656A of the elongated vessel 650 defines an interior chamber 658A of the elongated vessel 650.

Referring to FIG. 10, the first sidewall 652A of the elongated vessel 650 includes a through opening 659A fluidly connecting the interior chamber 658A of the elongated vessel 650 with an exterior of the elongated vessel 650. As illustrated in FIG. 10, the through opening 659A of the first sidewall 652A of the elongated vessel 650 overlaps a second through opening 610A of a first sidewall 602A of the container 600A, enabling the fiberoptic endoscopic examination cable 140 to travel from a second through opening 610A of the first sidewall 602A of the container 600A into the interior chamber 658A of the elongated vessel 650.

The elongated vessel 650 of the embodiment of FIG. 10 is a vessel that may be used to contain the flexible endoscopic cable 140 therein. This way, the flexible endoscopic cable 140 may be prevented from coming in direct contact with sidewalls 602A, 604A and/or 606A in the interior chamber 608A of the container 600A. In addition, the flexible endoscopic cable 140 can be straight when inserted in the interior chamber 608A, and the camera at the end of the flexible endoscopic cable 140 preferably does not contact any sidewall of the elongated vessel 650.

The sidewalls 602/602A, 604/604A, 606/606A of the container 600/600A may be made of a metal (e.g., aluminum, stainless steel, brass, or other suitable metals(s)), wood, an opaque elastomeric material, etc., or a combination thereof. The sidewalls 602/602A, 604/604A, 606/606A of the container 600/600A should be made of a material that blocks the transmission of UV light and has resistivity to structural degradation from exposure to UV light.

The elongated vessel 650 may be omitted from or may be provided in a container of the present disclosure, regardless of the shape and size of the container and regardless of the shape and size of the UV light source 908 inside of the container.

The switch 910 of the electrical circuit 900 may be a button switch (closing the circuit 900 upon being depressed), a rocker switch, a toggle switch, etc.

As illustrated in FIG. 5, the electrical wire 906 may enter the interior chamber 608 via a third through opening 620 in the first sidewall 602. Alternatively, the electrical wire 906 may enter the interior chamber 608 via a through opening located in any one of the other sidewalls 604, 606 of the container 600.

The first and second terminal ends 902, 904, of the electrical wire 906 may be embodied as prongs of a plug, as illustrated in FIG. 11. This way, the plug can be connected to a power outlet to receive electrical power.

Figure 7:
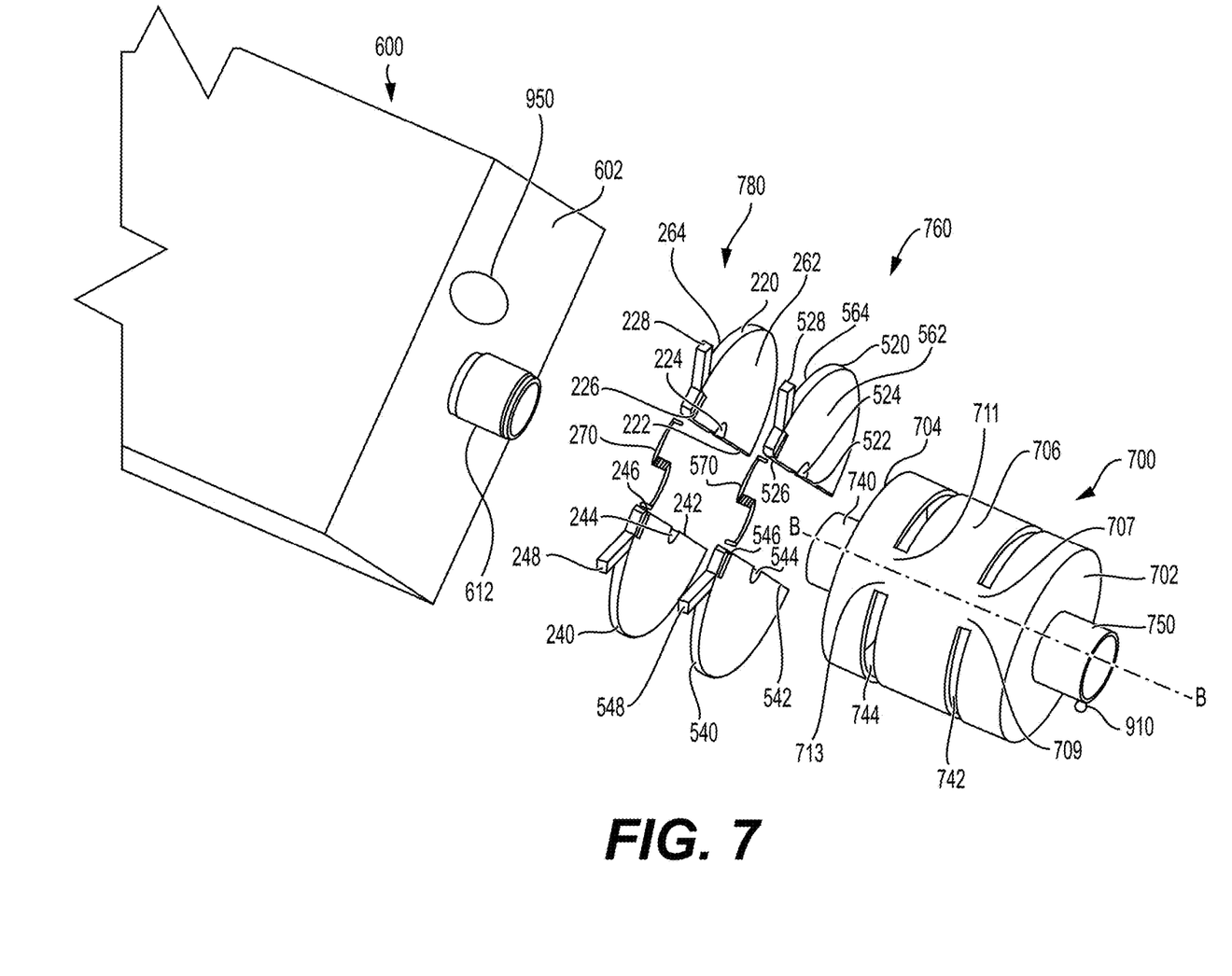
FIG. 7 is an exploded perspective view of a cleaning assembly included in the apparatus for sterilizing the endoscopic examination tool of FIG. 1.
Figure 8:
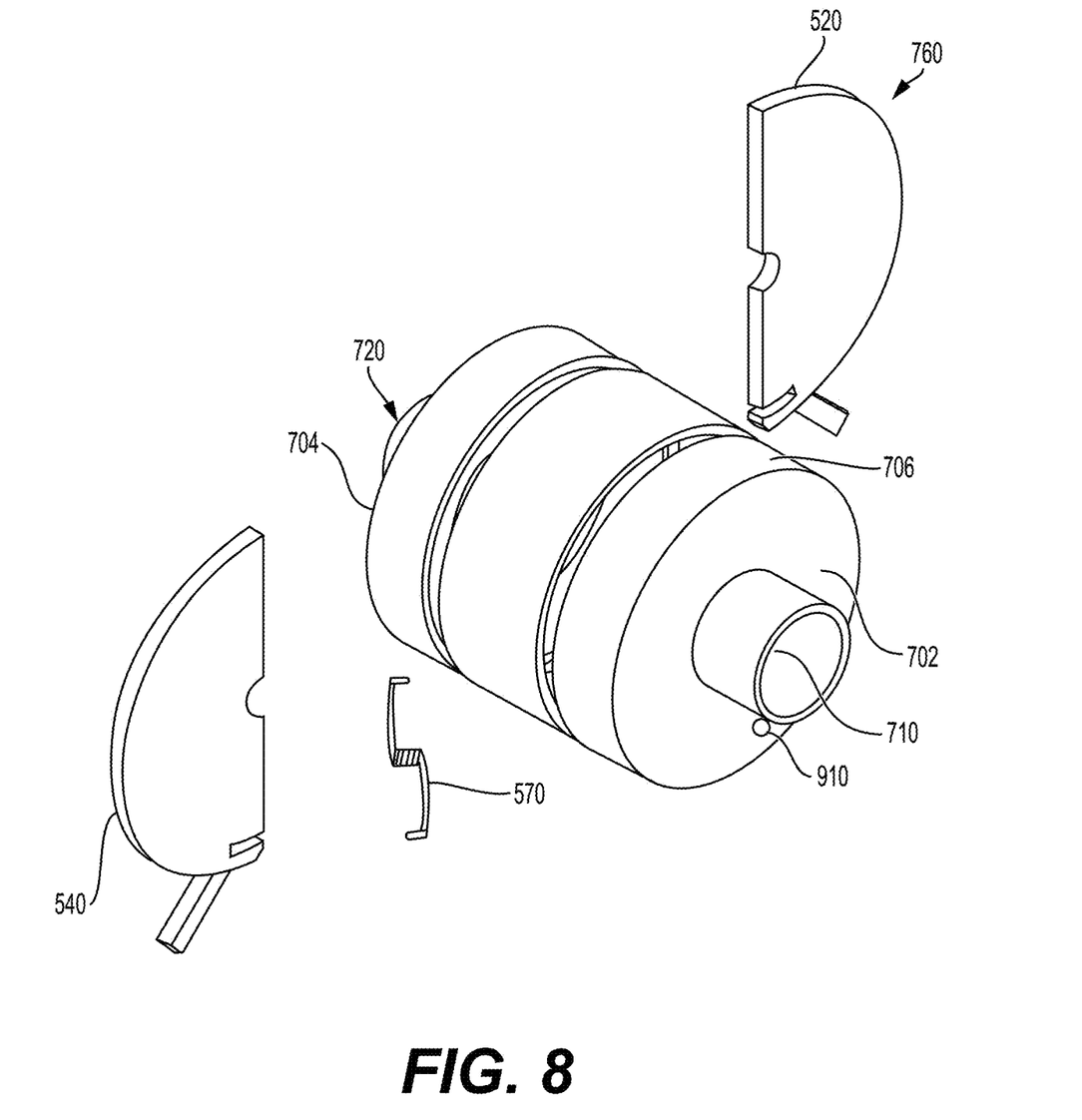
FIG. 8 is an exploded perspective view illustrating a portion of the cleaning assembly included in the apparatus for sterilizing the endoscopic examination tool of FIG. 1.

Referring to FIGS. 5 and 7, the cleaning assembly 700 has a first end 704, a second end 702 opposite to the first end 704, and a body 706 extending between the first and second ends 704, 702. The body 706 has a first through opening extending between the first end 704 and the second end 702.

Referring to FIG. 5, the first through opening of the body 706 forms a first opening 720 at the first end 704 of the body, a second opening 710 at the second end 702 of the body 706, and an interior chamber 730 of the body 706 between the first and second ends 704, 702.

The interior chamber 730 is in fluid communication with the first and second openings 720, 710 of the body 706.

Referring to FIG. 5, the cleaning assembly 700 may also include a hollow connecting piece 740 extending from the first end 704 of the body 706. The hollow connecting piece 740 may also be referred to as a "second" hollow connecting piece. The second hollow connecting piece 740 overlaps the first through opening 720 of the first end 704 of the body 706 of the cleaning assembly 700.

As illustrated in FIG. 5, the first and second hollow connecting pieces 612, 740 are connected to one another. The first and second hollow connecting pieces 612, 740 can be selectively (or removably) connected to one another. For example, the first and second hollow connecting pieces 612, 740 can form an interference fit (or friction fit) with one another. Other selective connection mechanism may include, for example, a threads on each of the first and second hollow connecting pieces 612, 740. For example, the inner first hollow connecting piece 612 may have threads on its exterior surface, and the outer second hollow connecting piece 740 may have matching threads on its inner surface. This way, the first and second hollow connecting pieces 612, 740 can be threadably connected to one another.

The first and second hollow connecting pieces 612, 740 can also be fixedly connected to one another.

FIG. 5 illustrates that the first hollow connecting piece 612 has a smaller diameter than the second hollow connecting piece 740 (and therefore, is inserted into the second hollow connecting piece 740). However, the present subject matter is not limited to this configuration. For example, the sizing of the first and second hollow connecting pieces 612, 740 can also be reversed. In the reversed arrangement, the first hollow connecting piece 612 would have a greater diameter than a diameter of the second hollow connecting piece 740. In this configuration, the second hollow connecting piece 740 would be inserted in the larger first hollow connecting piece 612 to selectively couple the container 600 with the cleaning assembly 700.

In a different embodiment of the present subject matter, an apparatus for sanitizing a fiberoptic endoscope may omit the first and second hollow connecting pieces 612, 740 altogether. In the embodiment where the first and second hollow connecting pieces 612, 740 are omitted, the first sidewall 602 of the container 600 may be directly connected to the first end 704 of the cleaning assembly 700 (or to a sidewall that defines the first end 704 of the body 706 of the cleaning assembly 700), with the second through opening 610 overlapping the first opening 720 of the cleaning assembly 700. The overlap between the second through opening 610 and the first opening 720 forms a passageway between the interior chamber 608 of the container and the interior chamber 730 of the body 706 of the cleaning assembly 700. The passageway enables the flexible endoscopic cable 140 to travel between the interior chamber 608 of the container and the interior chamber 730 of the body 706 of the cleaning assembly 700.

Referring to FIG. 5, the cleaning assembly 700 also include a hollow connecting piece 750 extending from the second end 702 of the body 706. The hollow connecting piece 750 may also be referred to as a "third" hollow connecting piece. The third hollow connecting piece 750 overlaps the second through opening 710 of the second end 702 of the body 706 of the cleaning assembly 700.

The third hollow connecting piece 750 defines the entry point of the flexible endoscopic cable 140 in the apparatus 500.

With reference to FIG. 5, the switch 910 may be disposed on the third hollow connecting piece 750. For example, the switch 910 may be disposed at a portion of the third hollow connecting piece 750 that is configured to contact the head portion 120 of the fiberoptic endoscope 100 when the fiberoptic endoscope 100 is coupled to the apparatus 500 (with the flexible endoscopic cable 140 inserted in the interior chamber 608 via the cleaning assembly 700). As illustrated in FIG. 5, the portion of the third hollow connecting piece 750 that is configured to contact the head portion 120 is a lip or rim of the connecting piece 750 located at an end of the connecting piece 750 that is distal to the body 706 of the cleaning assembly 700. This way, when the switch 910 is, for example, a button switch, the head portion 120 of the fiberoptic endoscope 100 may depress the button of the switch 910 when the fiberoptic endoscope 100 is coupled to the apparatus 500 for sanitization (e.g., due to the weight of the head portion 120 pressing the button when the flexible endoscopic cable 140 is inserted in the interior chamber 608/658A).

This configuration enables hand-free operation (e.g., turning on) of the UV light source 908 when the fiberoptic endoscope 100 is coupled to the apparatus 500. When the fiberoptic endoscope 100 is uncoupled from the apparatus 500, the button switch 910 returns to its normally open circuit position, turning off the UV light source 908. This configuration reduces energy consumption by turning on the UV light source 908 only when the examination tool 100 is coupled to the apparatus 500. In addition, this configuration does away with the need to manually turn on the UV light switch 908 subsequent to coupling the fiberoptic endoscope 100 with the apparatus 500.

In an embodiment, the third hollow connecting piece 750 of the cleaning assembly 700 may be omitted. In this embodiment, the flexible endoscopic cable 140 may be inserted in the cleaning assembly 700 via the second opening 710 of the body 706 of the cleaning assembly 700. In addition, in the embodiment where the third hollow connecting piece 750 is omitted, the button switch 910 may be disposed at an exterior portion of a sidewall that: a) forms the second end 702 of the body 706 of the cleaning assembly 700, and b) receives the head portion 120 of the fiberoptic endoscope 100 thereon when the fiberoptic endoscope 100 is coupled to the apparatus 500. Therefore, when the fiberoptic endoscope 100 is coupled to the apparatus 500, the head portion 120 when the flexible endoscopic cable 140 weighs over the button switch 910, causing the button switch 910 to close the electrical circuit 900.

The electrical circuit 900 is described in this specification as relying on an exterior source of power (such as the power grid of a building) to operate. However, the present subject matter is not limited to this configuration. The electrical circuit 900 may also include a power source electrically connected to the wire 906 for operating the UV lamp 908. The power source may be a rechargeable battery, for example, a lithium ion battery, etc. The power source may be included in the electrical circuit 900 in addition to the plug with the terminals 902, 904, or instead of the plug with the terminals 902, 904. The power source may be attached to the container 600.

Alternatively, the switch 910 may be disposed at any other location of the cleaning assembly 700 or the container 600. In this case, the switch 910 may be operated, for example, manually, to turn the UV light source on and off.

Referring to FIG. 7, the cleaning assembly 700 may include a first slit 742, a first plate 760 extending through the first slit 742 and selectively coupleable to the body 706, a second slit 744, and a second plate 780 extending through the second slit 744 and selectively coupleable to the body 706.

The first plate 760 is configured to disinfect the flexible endoscopic cable 140 by applying a disinfecting substance in fluid form to the exterior of the flexible endoscopic cable 140 while the flexible endoscopic cable 140 is passed through a central opening in the first plate 760.

As illustrated in FIG. 7, the first plate 760 may be the first plate, from among the plates 760, 780, that the flexible endoscopic cable 140 passes therethrough as the flexible endoscopic cable 140 is first inserted in the cleaning assembly 700, and subsequently, in the container 600.

The first plate 760 may have a disk-shape. Referring to FIG. 7, the first plate 760 may include a first plate component 520, a second plate component 540 and a first elastic member 570.

The first and second plate components 520, 540 may each have a half-disk shape. Referring to FIG. 7, the first plate component 520 includes a first mating side surface 522, a first notch 524 on the first mating side surface 522, a first cutout 526 on the first mating side surface 522 and a first protrusion 528.

The second plate component 540 may have a structural configuration that mirrors the configuration of the first plate component 520 about an imaginary plane that is parallel to the first mating side surface 522. Specifically, the second plate component 540 includes a second mating side surface 542, a second notch 544 on the second mating side surface 542, a second cutout 546 on the second mating side surface 542 and a second protrusion 548.

Referring to FIG. 7, when the first and second plate components 520 and 540 are disposed on one another to form the disk-like shape of the first plate 760, with the first and second mating side surfaces 522, 542 facing one another (or disposed on one another), the first and second plate components 520 and 540 together form a first side surface 562 the first plate 760, a second side surface 564 the first plate 760, opposite to the first side surface 562, and a first plate through hole 568 (see FIG. 4) that results from the combination of the first and second cutouts 524, 544 (i.e., when the first and second cutouts 524, 544 are aligned with one another and extend, or cut into the first and second plate components 520, 540, in opposite directions).

The first plate through hole 568 defines an interior sidewall of the first plate 760, and the cleaning substance may be disposed on the interior sidewall of the first plate 760, on the first side surface 562 of the first plate 760, and/or on the second side surface 564 of the first plate 760.

The cleaning substance may be, for example, chlorin dioxide $ClO_2$.

The first and second plate components 520 and 540 may be formed of an elastomeric material, and may be flexible in nature. For example, the first and second plate components 520 and 540 may be formed of synthetic rubber, natural rubber, polyester, polyurethane, vegetable cellulose etc. Each of the first and second plate components 520 and 540 may have a porous structure, akin to a sponge, or a substantially non-porous structure.

When the first and second plate components 520 and 540 are porous, the cleaning substance may be soaked into the pores of the first and second plate components 520 and 540 and may be present on their exterior side surfaces as well (i.e., the cleaning substance may be present on the first plate through hole 568 and on the first and second side surfaces 562, 564). When the first and second plate components 520 and 540 are substantially non-porous, the cleaning substance may be disposed on the first plate through hole 568 and/or on the first and second side surfaces 562, 564.

Therefore, whether the first and second plate components 520 and 540 are porous or substantially non-porous, the interior sidewall of the first plate the first plate 760 (defined by the first plate through hole 568) is configured to frictionally engage with the flexible endoscopic cable 140 when the flexible endoscopic cable 140 is fed through the interior of the cleaning assembly 700 to be disinfected after being used on a patient. The frictional engagement is configured to wipe bodily matter/fluids off the exterior of the flexible endoscopic cable 140 (along the length of the flexible endoscopic cable 140) and to deposit the cleaning substance of the exterior of the flexible endoscopic cable 140.

Therefore, the first plate 760 is configured to wipe and disinfect the flexible endoscopic cable 140 as the flexible endoscopic cable 140 is passed through the first plate 760.

Referring to FIG. 7, the first cutout 526 is configured to selectively receive a first portion 707 of the body 706 of the cleaning assembly 700 therein to selectively couple the first plate component 520 with the body 706 of the cleaning assembly 700. The first portion 707 is located above an imaginary line B-B in FIG. 7.

The second cutout 546 is configured to selectively receive a second portion 709 of the body 706 of the cleaning assembly 700 therein to selectively couple the second plate component 540 with the body 706 of the cleaning assembly 700. The second portion 709 is located below the imaginary line B-B in FIG. 7.

Figure 6:
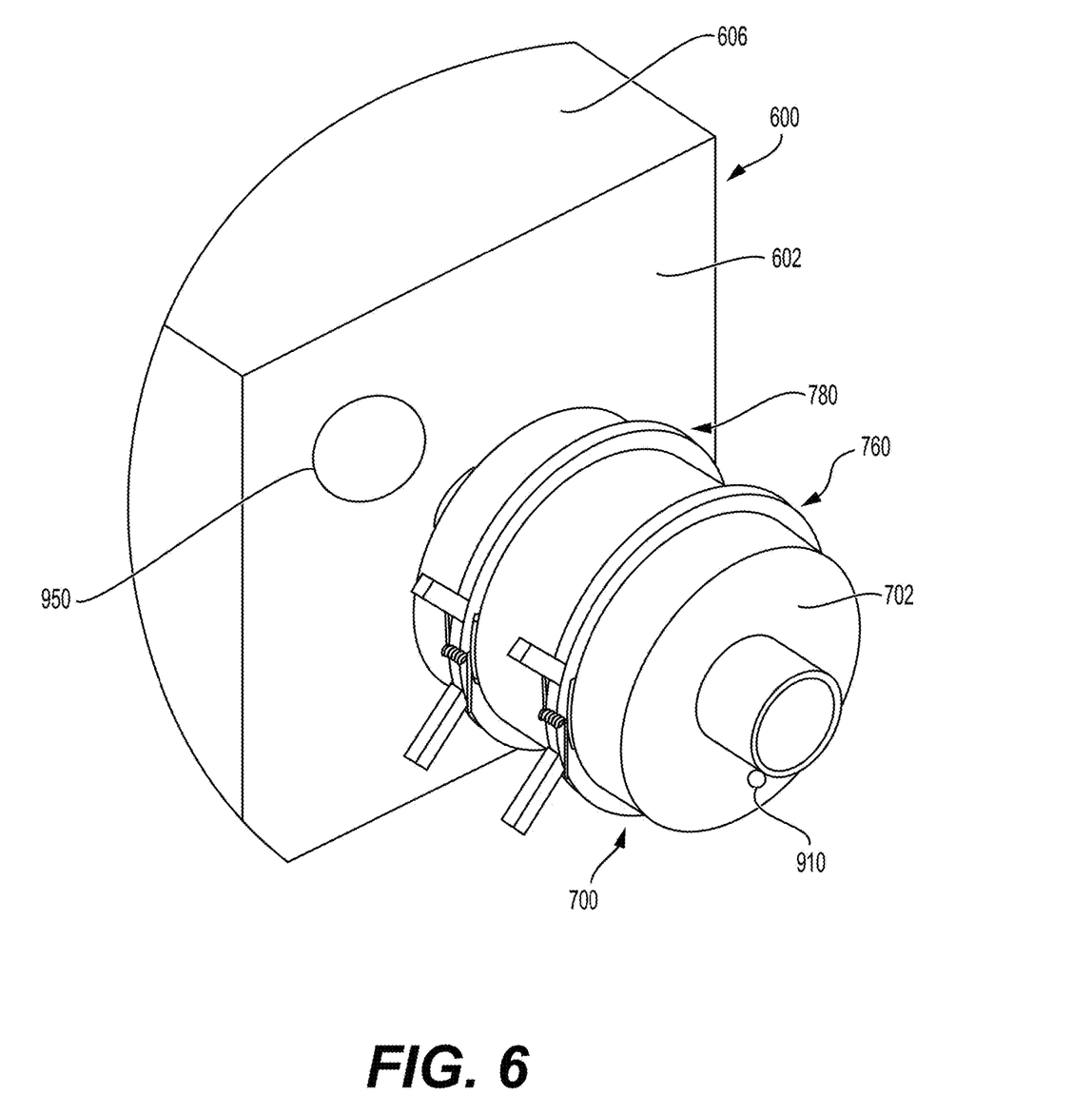
FIG. 6 is a magnified perspective view illustrating area A of FIG. 3.

As more clearly illustrated in FIG. 6, the first elastic member 570 may be selectively connected to the first and second protrusions 528, 548. The first elastic member 570 is configured to bias the first and second plate components 520, 540 toward one another when the first plate 760 is coupled to the body 706 of the cleaning assembly 700 to maintain the first and second plate components 520, 540 selectively and securely connected to the cleaning assembly 700.

The second plate 780 may have a shape that is similar to the shape of the first plate 760. However, the second plate 780 is configured to wipe the flexible endoscopic cable 140 as the flexible endoscopic cable 140 is passed through the second plate 780. The configuration of the cleaning assembly 700, and more specifically, with the first and second plates 760, 780 disposed sequentially and in-line with one another, ensures that the flexible endoscopic cable 140 is disinfected and wiped before entering the interior chamber 608 of the container 600 to be sterilized by an exposure to UV rays therein. In addition, the first plate through hole 568 and the second plate through hole may be arranged in-line with one another.

As illustrated in FIG. 7, the first plate 760 may be disposed between the second end 702 of the body 706 of the cleaning assembly 700 and the second plate 780. The second plate 780 may be disposed between the first plate 760 and the first end 704 of the body 706 of the cleaning assembly 700.

The second plate 780 may have a disk-shape. Referring to FIG. 7, the second plate 780 may include a first plate component 220, a second plate component 240 and a second elastic member 270.

The first and second plate components 220, 240 may each have a half-disk shape. Referring to FIG. 7, the first plate component 220 includes a first mating side surface 222, a first notch 224 on the first mating side surface 222, a first cutout 226 on the first mating side surface 222 and a first protrusion 228.

The second plate component 240 may have a structural configuration that mirrors the configuration of the first plate component 220 about an imaginary plane that is parallel to the first mating side surface 222. Specifically, the second plate component 240 includes a second mating side surface 242, a second notch 244 on the second mating side surface 242, a second cutout 246 on the second mating side surface 242 and a second protrusion 248.

Referring to FIG. 7, when the first and second plate components 220 and 240 are disposed on one another to form the disk-like shape of the first plate 760, with the first and second mating side surfaces 222, 242 facing one another (or disposed on one another), the first and second plate components 220 and 240 together form a first side surface 262 the second plate 780, a second side surface 264 the second plate 780, opposite to the first side surface 262, and a second plate through hole that results from the combination of the first and second cutouts 224, 244 (i.e., when the first and second cutouts 224, 244 are aligned with one another and extend, or cut into the first and second plate components 220, 240, in opposite directions).

The second plate through hole defines an interior sidewall of the second plate 780. A fabric material that is configured to wipe the exterior of the flexible endoscopic cable 140 may be disposed (e.g., attached, adhered, or otherwise formed) on the interior sidewall of the second plate 780, on the first side surface 262 and/or on the second side surface 264 of the second plate 780.

The fabric material may include fibers that are capable of wiping the exterior surface of flexible endoscopic cable 140 via frictional engagement when the flexible endoscopic cable 140 is passed through the interior sidewall of the second plate 780. The fabric material may include natural and/or synthetic fibers. The fabric material may include, for example, microfibers (or microfabric material), nylon fibers, polyester fibers, cotton fibers, etc., or blends thereof.

Therefore, the second plate 780 is configured to wipe the flexible endoscopic cable 140 as the flexible endoscopic cable 140 is passed through the second through hole of the second plate 780.

Referring to FIG. 7, the first cutout 226 is configured to selectively receive a third portion 711 of the body 706 of the cleaning assembly 700 therein to selectively couple the first plate component 220 with the body 706 of the cleaning assembly 700. The third portion 711 is located above the imaginary line B-B in FIG. 7.

The second cutout 246 is configured to selectively receive a fourth portion 713 of the body 706 of the cleaning assembly 700 therein to selectively couple the second plate component 240 with the body 706 of the cleaning assembly 700. The fourth portion 713 is located below the imaginary line B-B in FIG. 7.

As more clearly illustrated in FIG. 6, the second elastic member 270 may be selectively connected to the first and second protrusions 228, 248. The second elastic member 270 is configured to bias the first and second plate components 220, 240 toward one another when the second plate 780 is coupled to the body 706 of the cleaning assembly 700 to maintain the first and second plate components 220, 240 selectively and securely connected to the cleaning assembly 700.

As illustrated in FIGS. 5 and 7, the first plate through hole 568 and the second plate through hole can be arranged in line with the first and second openings 720, 710 of the body 706 of the cleaning assembly 700. This configuration facilitates the passing of the flexible endoscopic cable 140 between the cleaning assembly 700 and the container 600 for disinfecting and sterilizing the flexible endoscopic cable 140 after use.

The first and second plates 760, 780 may be single use or multi-use components of the apparatus 500. For example, the first and second plates 760, 780 may be replaceable after every use, after every two uses, etc. Each one of the first and second plates 760, 780 can be removed from the body 706 of the cleaning assembly 700 by uncoupling (or removing) its respective elastic member 570, 270, and then removing the first and second plate components 520, 540, 220, 240 from their respective slits 742, 744. New first and second plate components 520, 540, 220, 240 can be selectively connected to the body 706 of the cleaning assembly 700 by reversing the removal process. In addition, the first and second plates 760, 780 can be removed from the cleaning assembly 700 after the flexible endoscopic cable 140 has been sterilized and before the sterilized flexible endoscopic cable 140 is removed from the container 600.

The apparatus 500 may include a tag 950 disposed on the exterior of the container 600. The tag 950 may be, for example, a sticker adhered to the exterior of the container 600.

Referring to FIG. 9, the tag 950 may include visual indicia usable for calibrating the camera at the distal end of the flexible endoscopic cable 140. The tag 950 may include a two-dimensional geometric shape, a line, and/or text. Examples two-dimensional geometric shapes 952_1 to 952_N (with N being a positive nonzero integer) are illustrated in FIG. 9 for convenience of description. An example of a line is line 954, and an example of text is the text "TEST TEXT", illustrated in FIG. 9. It is understood that the number, size and/or shape of the geometric shapes 952_1 to 952_N, the size and/or shape of the line 954 and the size and/or content of the text 956 may be varied as needed.

The tag 950 can be used to calibrate the camera at the distal end 160 of the flexible endoscopic cable 140 by placing the distal end 160 of the flexible endoscopic cable 140 adjacent (or close) to the tag 950, and calibrating (e.g., adjusting the focal parameters) of the camera such that the video feed received by the camera of the flexible endoscopic cable 140 clearly depicts the geometric shapes 952_1 to 952_N, the line 954 and/or the text 956 displayed on the tag 950. The fiberoptic endoscope 100 is calibrated when the video feed of the camera depicts the geometric shapes 952_1 to 952_N, the line 954 and/or shape of the text 956 clearly.

Alternatively to being a sticker, or in addition to being a sticker, the tag 950 may be embodied as indicia printed (or otherwise displayed) directly on any one of the sidewalls 602, 604 and 606 of the container 600.

The present subject matter provides an apparatus 500 that can be used to sanitize and/or disinfect a fiberoptic endoscope quickly and efficiently by inserting the flexible endoscopic cable of the endoscope through the cleaning assembly 700 and through the container 600. In addition, the first and second plates 760, 780 have a configuration that enables them to be easily replaced in a physician's office with new plates. Moreover, the apparatus 500 can be manufactured at a low cost. Therefore, the apparatus 500 of the present subject matter can be used to do away with costly equipment that is otherwise needed to sterilize a flexible fiberoptic endoscope.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. An apparatus comprising:
a container including a plurality of sidewalls defining an exterior of the container and an interior chamber of the container; and
a cleaning assembly connected to the container,
wherein the cleaning assembly has a first end, a second end opposite to the first end, and a body extending between the first and second ends thereof, said body having a first through opening extending between the first end thereof and the second end thereof,
said first through opening forming:
a first opening at the first end of the body;
a second opening at the second end of the body; and
an interior chamber of the body between the first and second ends thereof,
the interior chamber of the body being in fluid communication with the first and second openings of the body,
wherein a first sidewall of the plurality of sidewalls of the container is connected to the first end of the body of the cleaning assembly,
wherein the first sidewall includes a second through opening, said second through opening overlapping the first opening at the first end of the body of the cleaning assembly, the overlap between the second through opening in the first sidewall and the first opening at the first end of the body of the cleaning assembly forming a passageway between the interior chamber of the container and the interior chamber of the body of the cleaning assembly,
wherein the interior chamber of the container and the interior chamber of the body of the cleaning assembly are configured to receive a fiberoptic endoscopic examination tool therein, said passageway being configured to accommodate said fiberoptic endoscopic examination tool therethrough.

2. The apparatus of claim 1, wherein the container further includes a first hollow connecting piece extending from the first sidewall thereof, the first hollow connecting piece overlapping the second through opening of the first sidewall of the container,
wherein the cleaning assembly further includes a second hollow connecting piece extending from the first end of the body thereof, the second hollow connecting piece overlapping the first opening at the first end of the body of the cleaning assembly, and
wherein the first and second hollow connecting pieces are connected to one another.

3. The apparatus of claim 2, wherein the first and second hollow connecting pieces are fixedly connected to one another.

4. The apparatus of claim 2, wherein the first and second hollow pieces are removably connected to one another.

5. The apparatus of claim 1, wherein the cleaning assembly further includes a first plate received in the interior chamber of the body,
wherein the first plate includes a first side surface, a second side surface opposite to the first side surface, and a first plate through hole, said first plate through hole extending between said first and second side surfaces of the first plate.

6. The apparatus of claim 5, wherein the first plate includes a cleaning substance disposed thereon.

7. The apparatus of claim 6, wherein the first plate through hole defines an interior sidewall of the first plate, and
wherein the cleaning substance is disposed on the interior sidewall of the first plate.

8. The apparatus of claim 6, wherein the first side surface of the first plate is arranged between the second end of the body of the cleaning assembly and the second side surface of the first plate, and
    wherein the cleaning substance is disposed on the first side surface of the first plate.
9. The apparatus of claim 6, wherein the first plate includes:
    a first plate component; and
    a second plate component,
    wherein the first plate component includes a first mating side surface and a first notch on the first mating side surface,
    wherein the second plate component includes a second mating side surface and a second notch on the second mating side surface,
    wherein the first and second mating surfaces are configured to be disposed on one another with the first and second notches aligned to form the first plate through hole.
10. The apparatus of claim 9, wherein the first plate component further includes a first cutout, the first cutout being configured to selectively receive a first portion of the body of the cleaning assembly therein to selectively couple the first plate component with the body of the cleaning assembly.
11. The apparatus of claim 10, wherein the second plate component further includes a second cutout, the second cutout being configured to selectively receive a second portion of the body of the cleaning assembly therein to selectively couple the second plate component with the body of the cleaning assembly.
12. The apparatus of claim 10, further comprising a first elastic member,
    wherein the first plate component includes a first protrusion extending from an exterior of the body of the cleaning assembly,
    wherein the second plate component includes a second protrusion extending from the exterior of the body of the cleaning assembly,
    wherein the first elastic member is connected to the first protrusion and to the second protrusion on the exterior of the body of the cleaning assembly, and
    wherein the first elastic member is configured to bias the first and second plate components toward one another.
13. The apparatus of claim 6, wherein the cleaning assembly further includes a second plate received in the interior chamber of the body, the second plate being disposed between the first plate and the first end of the body of the cleaning assembly,
    wherein the second plate includes a first side surface, a second side surface disposed opposite to the first side surface thereof, and a second plate through hole, said second plate through hole extending between the first and second side surfaces of the second plate.
14. The apparatus of claim 13, wherein the second plate through hole defines an interior sidewall of the second plate, and
    wherein the second plate includes a fabric material disposed on at least one selected from the group consisting of the interior sidewall of the second plate, the first side surface of the second plate and the second side surface of the second plate.
15. The apparatus of claim 13, wherein the first plate through hole and the second plate through hole are arranged in line with the first and second openings of the body of the cleaning assembly.
16. The apparatus of claim 13, further comprising an elongated vessel made of a transparent material, the elongated vessel being disposed in the interior chamber of the container and connected to the container,
    wherein the elongated vessel includes a first sidewall at a first end thereof, a second sidewall at a second end thereof, opposite to the first end thereof, and a hollow body extending between the first and second sidewalls thereof, the hollow body of the elongated vessel defining an interior chamber of the elongated vessel,
    wherein the first sidewall of the elongated vessel includes a through opening fluidly connecting the interior chamber of the elongated vessel with an exterior of the elongated vessel,
    wherein the through opening of the first sidewall of the elongated vessel overlaps the second through opening of the first sidewall of the container, enabling a fiberoptic examination cable of the fiberoptic endoscopic examination tool to travel from the second through opening of the sidewall of the container into the interior chamber of the elongated vessel.
17. The apparatus of claim 16, further comprising an ultraviolet (UV) light source disposed in the interior chamber of the container,
    wherein the UV light coils around the elongated member in a length direction of the elongated member.
18. The apparatus of claim 1, further comprising an ultraviolet (UV) light source disposed in the interior chamber of the container.
19. The apparatus of claim 18, further comprising a button switch disposed at the second end of the body of the cleaning assembly,
    said button switch configured to close an electrical circuit providing electrical power the UV light source upon being depressed.
20. The apparatus of claim 1, further comprising a tag disposed on the exterior of the container, the tag comprising at least one selected from the group consisting of a two-dimensional geometric shape, a line, and text, the tag being usable to calibrate the fiberoptic endoscopic examination tool.

* * * * *